(12) United States Patent
Radicone et al.

(10) Patent No.: US 7,329,385 B1
(45) Date of Patent: Feb. 12, 2008

(54) DEVICE AND METHOD FOR AIR STREAM, FLUID AND VESSEL DECONTAMINATION

(76) Inventors: Michael C. Radicone, 2528 Westlake Ave., Oceanside, NY (US) 11572; Lawrence S. Miller, 22 Vanderpost Crescent, Thornton, Ontario (CA) L0L 2N0

( * ) Notice: Subject to any disclaimer, the term of this patent is extended or adjusted under 35 U.S.C. 154(b) by 366 days.

(21) Appl. No.: 11/127,882

(22) Filed: May 12, 2005

Related U.S. Application Data

(60) Provisional application No. 60/586,332, filed on Jul. 8, 2004.

(51) Int. Cl.
*A61L 9/00* (2006.01)
(52) U.S. Cl. .............................. 422/4; 422/37; 422/122; 422/123; 96/227; 210/753
(58) Field of Classification Search ...................... None
See application file for complete search history.

(56) References Cited

U.S. PATENT DOCUMENTS

| | | | |
|---|---|---|---|
| 3,643,586 A | 2/1972 | Robinson | |
| 3,852,407 A | 12/1974 | Schmitt et al. | |
| 3,923,665 A | 12/1975 | Lambert et al. | |
| 3,958,026 A | 5/1976 | Leone et al. | |
| 4,088,640 A | 5/1978 | Detroit | |
| 4,208,396 A * | 6/1980 | Norman | 423/579 |
| 4,263,143 A * | 4/1981 | Ebner et al. | 210/629 |
| 4,343,765 A | 8/1982 | Elston et al. | |
| 4,642,192 A | 2/1987 | Heskett | |
| 5,135,654 A | 8/1992 | Heskett | |
| 5,230,624 A | 7/1993 | Wolf et al. | |
| 5,273,650 A * | 12/1993 | Vermes et al. | 210/264 |
| 5,344,558 A * | 9/1994 | Kool | 210/117 |
| 5,370,534 A | 12/1994 | Wolf et al. | |
| 5,401,399 A | 3/1995 | Magnusson et al. | |
| 5,474,451 A | 12/1995 | Dalrymple et al. | |
| 5,556,279 A | 9/1996 | Wolf et al. | |
| 5,562,824 A | 10/1996 | Magnusson | |
| 5,632,886 A * | 5/1997 | Staniec | 210/151 |
| 5,785,934 A | 7/1998 | Jacobs et al. | |
| 5,792,369 A | 8/1998 | Johnson | |
| 5,980,827 A * | 11/1999 | Messier | 422/37 |
| 6,036,738 A | 3/2000 | Shanbrom | |
| 2005/0011839 A1 | 1/2005 | Dart et al. | |

FOREIGN PATENT DOCUMENTS

| | | |
|---|---|---|
| JP | 01070060 | 3/1989 |
| JP | 2000227273 | 8/2000 |

\* cited by examiner

*Primary Examiner*—E. Leigh McKane
(74) *Attorney, Agent, or Firm*—Stites & Harbison, PLLC; David W. Nagle, Jr.; Mandy W. Decker

(57) ABSTRACT

A device for air stream, fluid and vessel decontamination generally comprises an air-inlet portion, through which air enters the device; an iodine-treatment portion; and a bubble-forming element through which iodine-laden air bubbles are released from the device into the fluid contained within the vessel. Such a device and related method substantially reduces, eliminates, or maintains microbial contamination of: air entering the device for release into the vessel; the fluid within the vessel; the interior surfaces of the vessel; and surfaces of any additional components coming into contact with the fluid or the air released from the device.

9 Claims, 2 Drawing Sheets

DEVICE AND METHOD FOR AIR STREAM, FLUID AND VESSEL DECONTAMINATION

CROSS-REFERENCE TO RELATED APPLICATIONS

The present application claims priority to U.S. Provisional Patent Application Ser. No. 60/586,332 filed July 8, 2004, the entire disclosure of which is incorporated herein by reference.

BACKGROUND OF THE INVENTION

The present invention relates to devices and methods for air stream, fluid and vessel decontamination, which may be used in association with a vessel containing a fluid relying on air for pressurization, agitation or aeration, for example, air-pressurized, self-contained water bottles used to provide dental-treatment water; pool or spa aeration devices using pressurized or venturi- drawn air; and air-injection devices used in waterfalls, fountains and pools.

Water or other fluids used for various applications may be held within a vessel and often rely on air for pressurization, agitation or aeration. Examples of such vessels include air-pressurized, self-contained water bottles used in dentistry to provide treatment water; pool or spa aeration devices using pressurized or venturi-drawn air; and air-injection devices used in waterfalls, fountains and pools. Because air must be drawn into these vessels, the fluid, as well as the interior of the vessel itself, is susceptible to microbial contamination by bacteria, viruses, mold and other airborne contaminants. Additionally, prior to entering the vessel, the fluid or the vessel may become contaminated, for example, as a result of mishandling. Such contaminations have the capacity to raise the fluid microbial counts above acceptable levels for a desired application. For example, the EPA standard for dental-treatment water is about 500 cfu/ml, and the above-mentioned contaminations could raise the fluid microbial counts above this level. Accordingly, there is a need in the art for a device and method which satisfactorily addresses the above-mentioned problems of fluid and vessel contamination.

SUMMARY OF THE INVENTION

The present invention addresses the above-identified problems, and others, by providing a device and method for air stream, fluid and vessel decontamination, which may be used in association with a vessel containing a fluid relying on air for pressurization, agitation or aeration.

An exemplary device made in accordance with the present invention generally comprises an air-inlet portion, through which air enters the device; an iodine-treatment portion; and a bubble-forming element through which iodine-laden air bubbles are released from the device into the fluid. Such a device substantially reduces, eliminates, or maintains microbial contamination of: air entering the device for release into the vessel; the fluid within the vessel; the interior surfaces of the vessel; and surfaces of any additional components coming into contact with the fluid or the air released from the device.

DETAILED DESCRIPTION OF THE INVENTION

The present invention is a device and method for air stream, fluid and vessel decontamination, which may be used in association with a vessel containing a fluid relying on air for pressurization, agitation or aeration, for example, air-pressurized, self-contained water bottles used to provide dental-treatment water; pool or spa aeration devices using pressurized or venturi- drawn air; and air-injection devices used in waterfalls, fountains and pools.

The device of the present invention infuses iodine molecules into the air stream entering the vessel, whether the air stream is pressurized or drawn, by treating it with iodine. The iodine treatment destroys substantially all of the microbes present within the air stream entering the vessel, preventing the introduction of microbial contamination via the air stream. As the iodine-treated air exits the device into the vessel, it percolates through the fluid contained within the vessel such that bubbles of iodine-laden air sublimate the iodine into the fluid to substantially eliminate, reduce, or maintain microbial counts at or below a predetermined level, depending on the application. These bubbles of iodine-laden air also form on the interior wall of the vessel, thereby treating microbial contamination of the vessel itself. Furthermore, where additional components are used in association with the fluid and the vessel (e.g., in a self-contained water bottle used for dental-treatment water, which includes additional components such as a bottle head, outlet tube, fittings and tubing), the additional components are treated for microbial contamination by the iodine-laden air bubbles. As such, microbial contamination of the fluid, the vessel, and additional components may also be addressed using the device of the present invention.

Figures 1, 2:
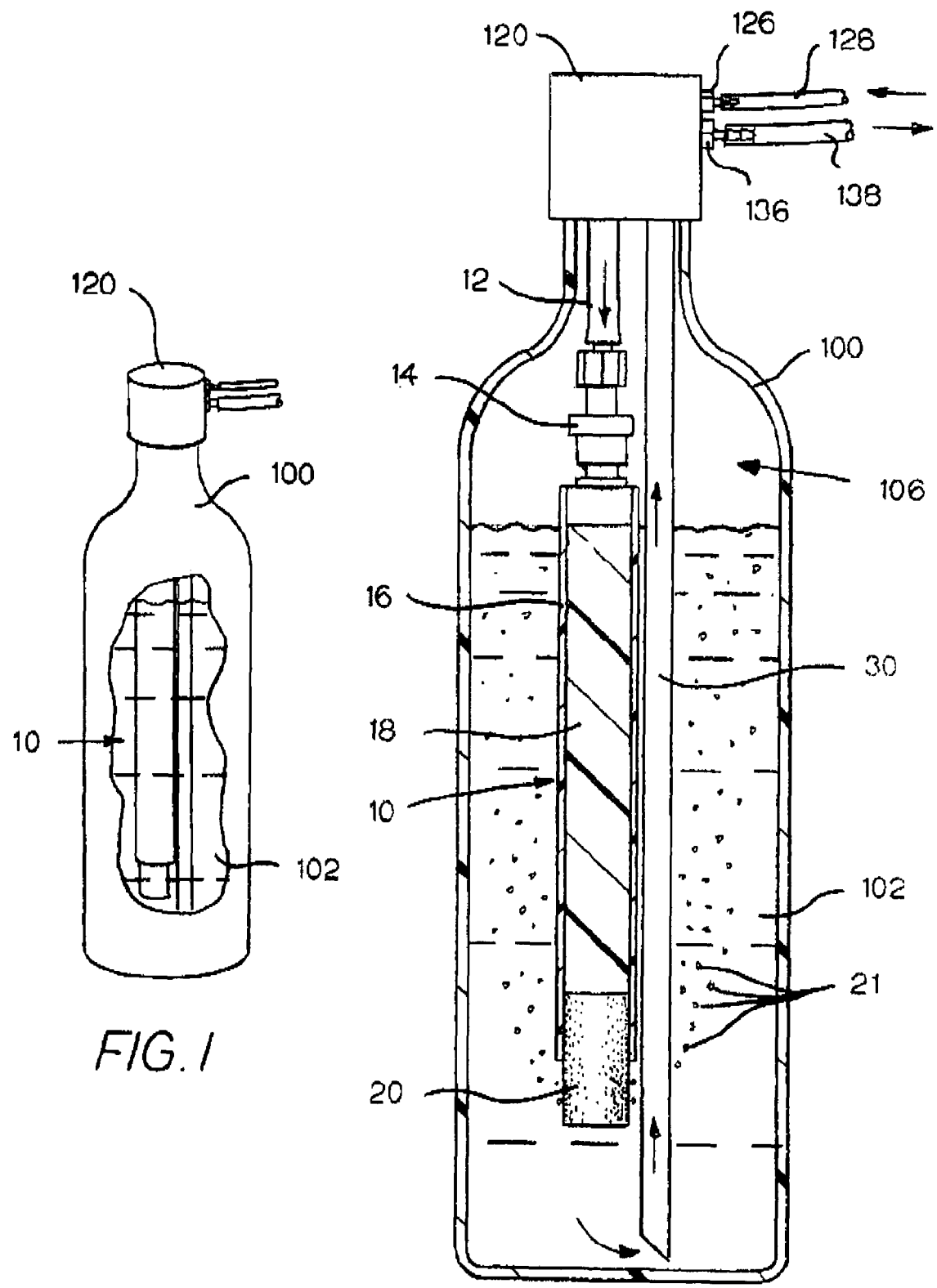
FIG. 1 is a perspective view of an exemplary device made in accordance with the present invention as inserted into a vessel of fluid.
FIG. 2 is an enlarged sectional view of the exemplary device of FIG. 1 as inserted into the vessel of fluid.
Figure 3:
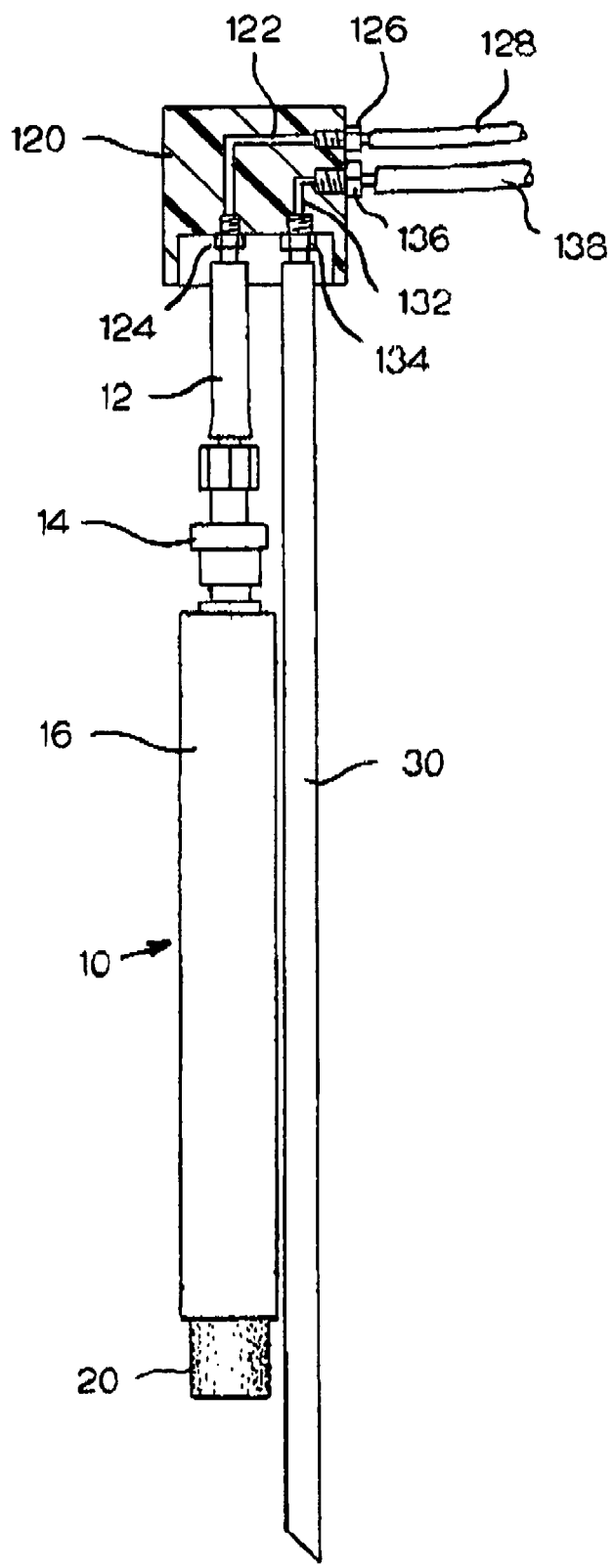
FIG. 3 is an alternate view of the exemplary device of FIG. 1, further illustrating the connection of the device to a cap that engages the open end of the vessel.

FIGS. 1-3 illustrate an exemplary device 10 made in accordance with the present invention, in this example, a device 10 that is inserted into a bottle 100 (i.e., the vessel) containing a fluid 102. The exemplary device 10 generally comprises an air-inlet portion 12, through which air enters the device 10; an iodine-treatment portion 16 in fluid communication with the air-inlet portion 14 for infusing the entering air stream with iodine ions; and a bubble-forming element 20 through which iodine-laden air bubbles 21 are released from the device 10 into the fluid 102. Furthermore, in this exemplary embodiment, the device 10 includes a check valve 14 interposed between the air-inlet portion 12 and the iodine-treatment portion 16 to prevent fluid from entering into the air-inlet portion 12.

Various commercially available iodine resins in crushed or small bead form (i.e., beads coated with iodine), or blends thereof, may be used in the iodine-treatment portion 16. In the exemplary embodiment illustrated in FIGS. 1-3, the iodine-treatment portion 16 is a substantially hollow and open-ended column packed with crushed and/or beaded iodine resin 18. For example, an iodine resin distributed by The Purolite Company of Bala Cynwyd, Pa. under Model No. 605, may be used in the exemplary device 10. The iodine resin 18 is held within the column 16 by the check valve 14 at the top end and the bubble-forming element 20 at the distal end of the column 16.

In any event, as air passes from the air-inlet portion 12, through the check valve 14 and into the column 16, the iodine resin 18 rapidly sublimates iodine ions into the air passing through the column 16, inactivating the exposed microbes in the air. Furthermore, during downtime, the column 16 acts as an air reservoir, extending the exposure to the iodine, facilitating the introduction of iodine ions into the air held within the column 16.

Iodine-laden air ultimately enters the bubble-forming element 20 at the distal end of the column 16. The bubble-forming element 20 is constructed from a porous material and provides active bubble formation. For example, an aquarium bubbler or airstone obtained from the Rolf C. Hagen (USA) Corporation of Mansfield, Mass. may be used as the bubble-forming element 20. In any event, the bubble-forming element 20 dispenses a flurry of iodine-laden air bubbles 21 into the fluid 102. It is contemplated that the bubble-forming element 20 may also contain an iodine resin, which produces a wicking action that prevents cross contamination by drawing fluid 102 up and into the iodine resin 18. Additionally, the presence of additional iodine resin within the bubble-forming element 20 further facilitates the introduction of iodine ions into the air passing therethrough.

As mentioned above, the iodine-laden air bubbles 21 sublimate the iodine into the fluid 102 substantially treating any microbial contamination that may be present in the fluid 102. Additionally, these bubbles 21 form on the interior walls of the bottle 100 to treat any microbial contamination that may be present on the walls of the bottle 100. Furthermore, iodine-laden bubbles 21 rise to the fluid surface and fill the space 106 defined between the fluid surface and the bottle 100 to treat any microbial contamination on the walls of the bottle 100 above the fluid surface. Still further, these bubbles 21 form on the surfaces of any additional components used in association with the device 10 and coming in contact with the bubble-containing fluid 102.

For example, in FIGS. 1-3, an outlet tube 30 is positioned within the bottle 100 for drawing fluid 102 from the bottle 100, for example, for dental treatment applications. Thus, the iodine-laden bubbles 21 come in contact with the surfaces of the outlet tube 30, as well as the surfaces of any downstream components, treating microbial contamination on these surfaces. As the fluid 102 is removed from the bottle 100 via the outlet tube 30, iodine-laden bubbles 21 continue to rise to the fluid surface and fill the space 106 defined by the fluid surface and the bottle 100 to treat any microbial contamination on the increasing surface of the walls of the bottle 100 above the fluid surface. Additionally, upon depletion of the fluid 102, the bottle 100 and associated outlet tube 30, or other associated components, may be purged with iodine-laden air to remove any remaining fluid 102 and reduce the susceptibility of microbial buildup on the walls of the bottle 100, the surfaces of the outlet tube 30, and/or other component surfaces.

Furthermore, in this particular example, and as illustrated in FIGS. 1-3, the device 10 and associated outlet tube 30 are both connected to a cap 120, which fits over and engages the open end of the bottle 100. As illustrated in FIG. 3, there is a first passageway 122 defined through the cap 120, allowing air from an external source to be delivered to the air-inlet portion 12 of the device 10. In this regard, a fitting 124 allows for connection of the air-inlet portion 12 at one end of the passageway 122, and a second fitting 126 at the opposite end of the passageway 122 allows for the connection of a tube 128 from the external air source. Similarly, there is also a second passageway 132 defined through the cap 120 with a fitting 134 that allows for connection of the outlet tube 30 at one end of the passageway 132, providing an exit for the fluid being drawn from the bottle 100. This passageway 132 terminates in a second fitting 136 adapted for connection to a tube 138 that delivers the fluid for the desired application, for example, to a dental handpiece.

The method of the present invention includes: infusing the air stream with iodine to create iodine-laden air substantially free of microbial contamination; forming bubbles of the iodine-laden air; and releasing the bubbles of the iodine-laden air into the fluid contained within the vessel for treating the fluid and vessel for contamination such that the fluid removed from the vessel has fluid microbial counts at or below a predetermined level based on the desired application.

One of ordinary skill in the art will also recognize that additional embodiments are possible without departing from the teachings of the present invention or the scope of the claims which follow. This detailed description, and particularly the specific details of the exemplary embodiment disclosed therein, is given primarily for clarity of understanding, and no unnecessary limitations are to be understood therefrom, for modifications will become obvious to those skilled in the art upon reading this disclosure and may be made without departing from the spirit or scope of the claimed invention.

What is claimed is:

1. A method for decontaminating an air stream, a fluid, and a vessel containing the fluid, comprising the steps of:
   infusing the air stream with iodine to create iodine-laden air by passing the air stream through a substantially hollow and open-ended column packed with crushed and/or beaded iodine resin;
   forming bubbles of the iodine-laden air; and
   releasing the bubbles of the iodine-laden air into the fluid contained within the vessel for decontaminating the fluid and vessel such that fluid removed from the vessel has fluid microbial counts at or below a predetermined level.

2. The method as recited in claim 1, in which forming and releasing bubbles of the iodine-laden air is achieved by providing a bubble-forming element at a distal end of the column.

3. The method as recited in claim 2, in which the bubble-forming element is an airstone.

4. The method as recited in claim 1, and further comprising the step of providing an outlet tube for drawing fluid from the vessel for a desired application.

5. A decontamination system, comprising:
   a vessel containing a fluid;
   a device inserted into the vessel and the fluid, including
      an air-inlet portion for receiving the air stream,
      a substantially hollow column packed with crushed and/or beaded iodine resin in fluid communication with the air-inlet portion for infusing the air stream with iodine ions, thereby decontaminating the air stream and creating iodine-laden air, and
      a bubble-forming element for forming and releasing bubbles of the iodine- laden air into the fluid contained within the vessel for decontaminating the fluid and vessel, such that fluid removed from the vessel has fluid microbial counts at or below a predetermined level; and
   a cap adapted to engage an open end of the vessel, said cap defining a first passageway for delivering air from an external source to the air-inlet portion of said device, and a second passageway for providing an exit for fluid being drawn from the vessel.

6. The system as recited in claim 5, in which said device further includes a check valve interposed between the air-inlet portion and the column for preventing the fluid contained within the vessel from entering the air-inlet portion.

7. The system as recited in claim 5, in which the bubble-forming element is positioned at a distal end of the column.

8. The system as recited in claim 7, in which the bubble-forming element is an airstone.

9. The system as recited in claim 5, and further comprising an outlet tube for drawing fluid from the vessel for a desired application.

* * * * *